(12) United States Patent
Peyrot et al.

(10) Patent No.: US 9,839,453 B2
(45) Date of Patent: Dec. 12, 2017

(54) OSTEOSYNTHESIS DEVICE

(71) Applicant: Stryker European Holdings I, LLC, Kalamazoo, MI (US)

(72) Inventors: Jacques Peyrot, Tassin la Demi Lune (FR); Tristan Meusnier, Saint-Etienne (FR); Bernard Prandi, Rennes (FR); Philippe Bellemere, Nantes (FR); Marc Augoyard, Tassin la Demi Lune (FR)

(73) Assignee: Stryker European Holdings I, LLC, Kalamazoo, MI (US)

( * ) Notice: Subject to any disclaimer, the term of this patent is extended or adjusted under 35 U.S.C. 154(b) by 382 days.

(21) Appl. No.: 13/686,074

(22) Filed: Nov. 27, 2012

(65) Prior Publication Data

US 2014/0039630 A1    Feb. 6, 2014

Related U.S. Application Data

(63) Continuation of application No. 12/531,577, filed as application No. PCT/FR2008/050453 on Mar. 14, 2008, now Pat. No. 8,394,097.

(30) Foreign Application Priority Data

Mar. 20, 2007    (FR) ..................................... 07 02003

(51) Int. Cl.
 *A61B 17/04* (2006.01)
 *A61B 17/84* (2006.01)
 (Continued)

(52) U.S. Cl.
 CPC .......... *A61B 17/72* (2013.01); *A61B 17/7266* (2013.01); *A61B 17/7283* (2013.01);
 (Continued)

(58) Field of Classification Search
 CPC ........................... A61B 17/72; A61B 17/7233
 (Continued)

(56) References Cited

U.S. PATENT DOCUMENTS 1,095,054 A    4/1914    Wiesenfeld
3,462,765 A    8/1969    Swanson
(Continued)

FOREIGN PATENT DOCUMENTS

CA    2551021 A1    3/2005
CA    2243699 C    1/2006
(Continued)

OTHER PUBLICATIONS

International Search Report for PCT/FR2008/050453 dated Nov. 4, 2008.
(Continued)

*Primary Examiner* — David Isabella
*Assistant Examiner* — Christine Nelson
(74) *Attorney, Agent, or Firm* — Lerner, David, Littenberg, Krumholz & Mentlik, LLP

(57) ABSTRACT

In one embodiment, the present invention includes an intramedullary osteosynthesis or arthrodesis implant including a central body, a first pair of legs extending from the central body to a pair of leg tips, and a second pair of legs extending from the central body, in a direction opposite the first pair of legs, to a pair of leg tips such that the central body, first pair of legs and second pair of legs are positioned alongside a longitudinal axis.

20 Claims, 6 Drawing Sheets

(51) Int. Cl.
*A61F 2/08* (2006.01)
*A61B 17/72* (2006.01)
*A61F 2/42* (2006.01)
*A61F 2/30* (2006.01)

(52) U.S. Cl.
CPC ............ *A61B 17/7291* (2013.01); *A61F 2/30* (2013.01); *A61F 2/4241* (2013.01); *A61B 17/7225* (2013.01); *A61F 2002/30092* (2013.01); *A61F 2002/30166* (2013.01); *A61F 2002/30179* (2013.01); *A61F 2002/30563* (2013.01); *A61F 2002/30622* (2013.01); *A61F 2002/30841* (2013.01); *A61F 2002/4243* (2013.01); *A61F 2210/0014* (2013.01); *A61F 2230/0028* (2013.01); *A61F 2230/0058* (2013.01); *A61F 2310/00023* (2013.01)

(58) Field of Classification Search
USPC ..................................................... 606/62, 63
See application file for complete search history.

(56) References Cited

U.S. PATENT DOCUMENTS

| | | |
|---|---|---|
| 3,466,669 A | 9/1969 | Flatt |
| 3,593,342 A | 7/1971 | Niebauer et al. |
| 3,681,786 A | 8/1972 | Lynch |
| 3,739,403 A | 6/1973 | Nicolle |
| 3,805,302 A | 4/1974 | Mathys |
| 3,824,631 A | 7/1974 | Burstein et al. |
| 3,875,594 A | 4/1975 | Swanson |
| D243,716 S | 3/1977 | Treace et al. |
| 4,091,806 A | 5/1978 | Aginsky et al. |
| 4,158,893 A | 6/1979 | Swanson |
| 4,204,284 A | 5/1980 | Koeneman |
| 4,276,660 A | 7/1981 | Laure |
| 4,364,382 A | 12/1982 | Mennen |
| 4,367,562 A | 1/1983 | Gauthier et al. |
| D277,509 S | 2/1985 | Lawrence et al. |
| D277,784 S | 2/1985 | Sgarlato et al. |
| 4,522,200 A | 6/1985 | Stednitz |
| D284,099 S | 6/1986 | Laporta et al. |
| 4,634,382 A | 1/1987 | Kusano et al. |
| D291,731 S | 9/1987 | Aikins |
| 4,759,768 A | 7/1988 | Hermann et al. |
| 4,871,367 A | 10/1989 | Christensen et al. |
| 4,955,916 A | 9/1990 | Carignan et al. |
| 4,969,909 A | 11/1990 | Barouk |
| 5,011,497 A | 4/1991 | Persson et al. |
| 5,047,059 A | 9/1991 | Saffar |
| 5,062,851 A | 11/1991 | Branemark |
| 5,092,896 A | 3/1992 | Meuli et al. |
| 5,108,443 A | 4/1992 | Branemark |
| 5,133,761 A | 7/1992 | Krouskop |
| 5,179,915 A | 1/1993 | Cohen et al. |
| 5,190,546 A | 3/1993 | Jervis |
| 5,207,712 A | 5/1993 | Cohen |
| 5,326,364 A | 7/1994 | Clift, Jr. et al. |
| 5,360,450 A | 11/1994 | Giannini |
| 5,405,400 A | 4/1995 | Linscheid et al. |
| 5,405,401 A | 4/1995 | Lippincott, III et al. |
| 5,425,776 A | 6/1995 | Cohen |
| 5,425,777 A | 6/1995 | Sarkisian et al. |
| 5,454,814 A * | 10/1995 | Comte ............... A61B 17/0642 606/219 |
| 5,464,427 A | 11/1995 | Curtis et al. |
| 5,474,557 A | 12/1995 | Mai |
| 5,480,447 A | 1/1996 | Skiba |
| 5,484,443 A | 1/1996 | Pascarella et al. |
| 5,507,822 A | 4/1996 | Bouchon et al. |
| 5,522,903 A | 6/1996 | Sokolow et al. |
| 5,554,157 A | 9/1996 | Errico et al. |
| 5,634,925 A | 6/1997 | Urbanski |
| 5,674,297 A | 10/1997 | Lane et al. |
| 5,702,472 A | 12/1997 | Huebner |
| 5,725,585 A | 3/1998 | Zobel |
| 5,782,927 A | 7/1998 | Klawitter et al. |
| 5,824,095 A | 10/1998 | Di Maio, Jr. et al. |
| 5,876,434 A | 3/1999 | Flomenblit et al. |
| 5,882,444 A | 3/1999 | Flomenblit et al. |
| 5,919,193 A | 7/1999 | Slavitt |
| 5,951,288 A | 9/1999 | Sawa |
| 5,958,159 A | 9/1999 | Prandi |
| 5,984,970 A | 11/1999 | Bramlet |
| 5,984,971 A | 11/1999 | Faccioli et al. |
| 6,011,497 A | 1/2000 | Tsang et al. |
| 6,017,366 A | 1/2000 | Berman |
| 6,146,387 A | 11/2000 | Trott et al. |
| 6,162,234 A | 12/2000 | Freedland et al. |
| 6,193,757 B1 | 2/2001 | Foley et al. |
| 6,197,037 B1 | 3/2001 | Hair |
| 6,200,330 B1 | 3/2001 | Benderev et al. |
| 6,248,109 B1 | 6/2001 | Stoffella |
| 6,261,289 B1 | 7/2001 | Levy |
| 6,319,284 B1 | 11/2001 | Rushdy et al. |
| 6,342,076 B1 | 1/2002 | Lundborg |
| 6,352,560 B1 | 3/2002 | Poeschmann et al. |
| 6,383,223 B1 | 5/2002 | Baehler et al. |
| 6,386,877 B1 | 5/2002 | Sutter |
| 6,423,097 B2 | 7/2002 | Rauscher |
| 6,428,634 B1 | 8/2002 | Besselink et al. |
| 6,454,808 B1 | 9/2002 | Masada |
| 6,475,242 B1 | 11/2002 | Bramlet |
| 6,554,833 B2 | 4/2003 | Levy et al. |
| 6,689,169 B2 | 2/2004 | Harris |
| 6,699,247 B2 | 3/2004 | Zucherman et al. |
| 6,699,292 B2 | 3/2004 | Ogilvie et al. |
| 6,706,045 B2 | 3/2004 | Lin et al. |
| 6,773,437 B2 | 8/2004 | Ogilvie et al. |
| 6,811,568 B2 | 11/2004 | Minamikawa |
| 6,827,741 B2 | 12/2004 | Reeder |
| 6,869,449 B2 | 3/2005 | Ball et al. |
| 6,896,177 B2 | 5/2005 | Carter |
| 6,981,974 B2 | 1/2006 | Berger |
| 7,025,789 B2 | 4/2006 | Chow et al. |
| 7,037,342 B2 | 5/2006 | Nilsson et al. |
| 7,041,106 B1 | 5/2006 | Carver et al. |
| 7,052,498 B2 | 5/2006 | Levy et al. |
| 7,182,787 B2 | 2/2007 | Hassler et al. |
| 7,240,677 B2 | 7/2007 | Fox |
| 7,291,175 B1 | 11/2007 | Gordon |
| 7,588,603 B2 | 9/2009 | Leonard |
| 7,655,042 B2 | 2/2010 | Foley et al. |
| 7,780,737 B2 | 8/2010 | Bonnard et al. |
| 7,837,738 B2 | 11/2010 | Reigstad et al. |
| 7,842,091 B2 | 11/2010 | Johnstone et al. |
| 7,909,880 B1 | 3/2011 | Grant |
| 7,922,765 B2 | 4/2011 | Reiley |
| 7,955,388 B2 | 6/2011 | Jensen et al. |
| 7,976,580 B2 | 7/2011 | Berger |
| 8,048,173 B2 | 11/2011 | Ochoa |
| 8,100,983 B2 | 1/2012 | Schulte |
| 8,162,942 B2 | 4/2012 | Coati et al. |
| 8,202,305 B2 | 6/2012 | Reiley |
| 8,262,712 B2 | 9/2012 | Coilard-Lavirotte et al. |
| 8,308,779 B2 | 11/2012 | Reiley |
| 8,394,097 B2 | 3/2013 | Peyrot et al. |
| 8,414,583 B2 | 4/2013 | Prandi et al. |
| 8,475,456 B2 | 7/2013 | Augoyard et al. |
| 8,529,611 B2 | 9/2013 | Champagne et al. |
| 8,597,337 B2 | 12/2013 | Champagne |
| 8,608,785 B2 | 12/2013 | Reed et al. |
| 8,685,024 B2 | 4/2014 | Roman |
| 8,715,325 B2 | 5/2014 | Weiner et al. |
| 8,840,623 B2 | 9/2014 | Reiley |
| 8,864,804 B2 | 10/2014 | Champagne et al. |
| 9,011,504 B2 | 4/2015 | Reed |
| 9,283,007 B2 | 3/2016 | Augoyard et al. |
| 2001/0025199 A1 | 9/2001 | Rauscher |
| 2002/0019636 A1 | 2/2002 | Ogilvie et al. |
| 2002/0055785 A1 | 5/2002 | Harris |
| 2002/0065561 A1 | 5/2002 | Ogilvie et al. |
| 2002/0068939 A1 | 6/2002 | Levy et al. |

(56) References Cited

U.S. PATENT DOCUMENTS

| | | |
|---|---|---|
| 2002/0082705 A1 | 6/2002 | Bouman et al. |
| 2002/0169066 A1 | 11/2002 | Cassidy et al. |
| 2003/0040805 A1 | 2/2003 | Minamikawa |
| 2003/0069645 A1 | 4/2003 | Ball et al. |
| 2003/0120277 A1 | 6/2003 | Berger |
| 2003/0130660 A1* | 7/2003 | Levy et al. ............... 606/63 |
| 2004/0002759 A1 | 1/2004 | Ferree |
| 2004/0093081 A1 | 5/2004 | Nilsson et al. |
| 2004/0102853 A1 | 5/2004 | Boumann et al. |
| 2004/0138756 A1 | 7/2004 | Reeder |
| 2004/0220678 A1 | 11/2004 | Chow et al. |
| 2005/0119757 A1 | 6/2005 | Hassler et al. |
| 2005/0251265 A1 | 11/2005 | Calandruccio et al. |
| 2005/0261768 A1* | 11/2005 | Trieu ............... A61B 17/7065 623/17.11 |
| 2005/0283159 A1* | 12/2005 | Amara ............... A61B 17/7266 606/75 |
| 2006/0052725 A1 | 3/2006 | Santilli |
| 2006/0052878 A1 | 3/2006 | Schmieding |
| 2006/0074492 A1 | 4/2006 | Frey |
| 2006/0084998 A1 | 4/2006 | Levy et al. |
| 2006/0085075 A1 | 4/2006 | McLeer |
| 2006/0247787 A1 | 11/2006 | Rydell et al. |
| 2007/0038303 A1 | 2/2007 | Myerson et al. |
| 2007/0123993 A1 | 5/2007 | Hassler et al. |
| 2007/0142920 A1 | 6/2007 | Niemi |
| 2007/0156241 A1 | 7/2007 | Reiley et al. |
| 2007/0185584 A1 | 8/2007 | Kaufmann et al. |
| 2007/0213831 A1 | 9/2007 | de Cubber |
| 2007/0239158 A1 | 10/2007 | Trieu et al. |
| 2008/0039949 A1 | 2/2008 | Meesenburg et al. |
| 2008/0132894 A1 | 6/2008 | Coilard-Lavirotte et al. |
| 2008/0154385 A1 | 6/2008 | Trail et al. |
| 2008/0177262 A1 | 7/2008 | Augoyard et al. |
| 2008/0195219 A1 | 8/2008 | Wiley et al. |
| 2008/0221697 A1 | 9/2008 | Graser |
| 2008/0221698 A1 | 9/2008 | Berger |
| 2008/0234763 A1 | 9/2008 | Patterson et al. |
| 2008/0269908 A1 | 10/2008 | Warburton |
| 2009/0005821 A1 | 1/2009 | Chirico et al. |
| 2009/0012564 A1 | 1/2009 | Chirico et al. |
| 2009/0138096 A1 | 5/2009 | Myerson et al. |
| 2009/0254189 A1 | 10/2009 | Scheker |
| 2009/0254190 A1 | 10/2009 | Gannoe et al. |
| 2010/0010637 A1 | 1/2010 | Pequignot |
| 2010/0016905 A1 | 1/2010 | Greenhalgh et al. |
| 2010/0016982 A1 | 1/2010 | Solomons |
| 2010/0057214 A1 | 3/2010 | Graham et al. |
| 2010/0121390 A1 | 5/2010 | Kleinman |
| 2010/0131014 A1 | 5/2010 | Peyrot |
| 2010/0131072 A1 | 5/2010 | Schulte |
| 2010/0161068 A1 | 6/2010 | Lindner et al. |
| 2010/0185295 A1 | 7/2010 | Emmanuel |
| 2010/0228301 A1 | 9/2010 | Greenhalgh et al. |
| 2010/0249942 A1 | 9/2010 | Goswami et al. |
| 2010/0256770 A1 | 10/2010 | Hakansson et al. |
| 2010/0262254 A1 | 10/2010 | Lawrence et al. |
| 2011/0004317 A1 | 1/2011 | Hacking et al. |
| 2011/0093084 A1 | 4/2011 | Morton |
| 2011/0093085 A1 | 4/2011 | Morton |
| 2011/0144644 A1 | 6/2011 | Prandi et al. |
| 2011/0301652 A1 | 12/2011 | Reed et al. |
| 2012/0029579 A1 | 2/2012 | Bottlang et al. |
| 2012/0065692 A1 | 3/2012 | Champagne et al. |
| 2013/0053975 A1 | 2/2013 | Reed et al. |
| 2013/0060295 A1 | 3/2013 | Reed et al. |
| 2013/0066435 A1 | 3/2013 | Averous et al. |
| 2013/0131822 A1 | 5/2013 | Lewis et al. |
| 2013/0150965 A1 | 6/2013 | Taylor et al. |
| 2014/0058462 A1 | 2/2014 | Reed et al. |
| 2014/0142715 A1 | 5/2014 | McCormick |
| 2014/0180428 A1 | 6/2014 | McCormick |
| 2014/0188239 A1 | 7/2014 | Cummings |

FOREIGN PATENT DOCUMENTS

| | | | |
|---|---|---|---|
| CA | 2836654 A1 | 6/2014 | |
| CA | 2837497 A1 | 6/2014 | |
| EP | 0042808 A1 | 12/1981 | |
| EP | 0420794 A1 | 4/1991 | |
| EP | 0454645 A1 | 10/1991 | |
| EP | 1300122 A2 | 4/2003 | |
| EP | 1356794 A3 | 11/2003 | |
| EP | 1582159 A1 | 10/2005 | |
| EP | 1923012 A1 | 5/2008 | |
| FR | 2663838 A1 | 1/1992 | |
| FR | 2725126 A1 | 4/1996 | |
| FR | 2783702 A1 | 3/2000 | |
| FR | 2787313 A1 | 6/2000 | |
| FR | 2794019 A1 | 12/2000 | |
| FR | 2801189 A1 | 5/2001 | |
| FR | 2846545 A | 5/2004 | |
| FR | 2846545 A1 | 5/2004 | |
| FR | 2884406 | 10/2006 | |
| FR | EP 1 923 012 A1 * | 11/2006 | ............. A61B 17/72 |
| GB | 2119655 A | 11/1983 | |
| GB | 2430625 A | 4/2007 | |
| GB | 2430625 B | 4/2007 | |
| JP | 60145133 A | 7/1985 | |
| JP | 03-001854 A | 8/1991 | |
| JP | 7303662 A | 11/1995 | |
| JP | 2004535249 A | 11/2004 | |
| JP | 3648687 B2 | 5/2005 | |
| JP | 2007530194 A | 11/2007 | |
| JP | 2008188411 A | 8/2008 | |
| JP | 2008537696 A | 9/2008 | |
| JP | 4695511 B2 | 6/2011 | |
| JP | 5631597 B2 | 11/2014 | |
| KR | 20070004513 A | 1/2007 | |
| KR | 20070022256 A | 2/2007 | |
| KR | 101004561 B1 | 1/2011 | |
| KR | 101235983 B1 | 2/2013 | |
| WO | 9116014 A1 | 10/1991 | |
| WO | 9625129 A1 | 8/1996 | |
| WO | 9641596 A1 | 12/1996 | |
| WO | 9726846 A1 | 7/1997 | |
| WO | 9733537 A1 | 9/1997 | |
| WO | 0117445 A1 | 3/2001 | |
| WO | 03084416 A1 | 10/2003 | |
| WO | 2005020830 A1 | 3/2005 | |
| WO | 2005063149 A1 | 7/2005 | |
| WO | 2005104961 A1 | 11/2005 | |
| WO | 2006109004 A1 | 10/2006 | |
| WO | 2008057404 A2 | 5/2008 | |
| WO | 2008112308 A1 | 9/2008 | |
| WO | 2009103085 A1 | 8/2009 | |
| WO | 2011130229 A1 | 10/2011 | |

OTHER PUBLICATIONS

International Search Report, PCT/FR2006/050345, dated Aug. 30, 2006.

* cited by examiner

OSTEOSYNTHESIS DEVICE

CROSS-REFERENCE TO RELATED APPLICATIONS

This application is a continuation of U.S. application Ser. No. 12/531,577, filed Feb. 1, 2010, which is a national phase entry under 35 U.S.C. §371 of International Application No. PCT/FR2008/050453 filed Mar. 14, 2008, published in French, which claims priority from FR 0702003 filed Mar. 20, 2007, all of which are hereby incorporated herein by reference.

FIELD OF THE INVENTION

The invention relates to the technical field of orthopaedic implants, in particular for arthrodeses and osteosyntheses.

BACKGROUND OF THE INVENTION

It may be recalled that an osteosynthesis implant must serve to hold in place two (or more) parts of the same bone fractured or cut by a surgical operation (osteotomy), for the time necessary for the consolidation of this bone (typically 3 months).

It may be recalled that an arthrodesis is the blocking of a joint by surgery to fuse two bones into a single one, using an osteosynthesis device.

It may be recalled that the purpose of any osteosynthesis and particularly in the case of an arthrodesis is to obtain very good primary and also secondary stability, in order to obtain the consolidation in the best possible conditions, that is, in a position selected by the surgeon, by minimizing the problems of post-operative pain and edemas, by shortening the consolidation time as much as possible.

To obtain this result, the stability of the osteosynthesis associated with the implant is critical. Furthermore, the implant must also provide and maintain a slight compression on the portions of bone to be fused together, thereby facilitating this consolidation.

Various technical solutions have been proposed to carry out an arthrodesis, in particular at the tips (foot, hand, wrist, ankle, etc.).

Mention can be made, for example of basic staples which do not provide a proper fixation during consolidation, and shape memory staples which serve to place the two bone portions to be consolidated under compression, thereby corresponding to the intended purpose.

However, to obtain satisfactory stability, it is necessary to place two, or even three staples, in different planes. This significantly increases their size, thereby limiting the applications, in particular on small bones (for example in the fingers or toes).

It is also common to use extramedullary or extra-osseous plates and screws, which also require a relatively large space and cannot be used on the terminal phalanges of the fingers (distal interphalangeal arthrodesis for example). Moreover, the medium-term stability of these systems is not always guaranteed (loosening of the mounting).

Certain types of screw can be used in intramedullary cases, but in this case, the approach path requires a pulpar approach, which may generate serious complications (sepsis, etc.) and discomfort for the patient.

Use can also be made of pins which have a smaller size. However, the stability obtained is not satisfactory (problems of migration) and it is generally necessary to remove them after consolidation. With such devices, moreover, the patient cannot immerse the finger or toe treated, because the pin generally projects outside the skin.

Intramedullary osteosynthesis systems are available for long bones (tibia, femur, humerus, etc.). For example, lockable centromedullary nails are known. Apart from the fact that the locking technique is difficult, it cannot be miniaturized for extremity surgery (hand and foot).

Shape memory intramedullary devices are also available for solving part of the problems with respect to the arthrodesis or the osteosynthesis of the small fragments: for example, the solutions described in French patent 2 846 545 or French patent 2 884 406 (U.S. 2008/0177262).

French Patent 2 846 545 describes an H-shaped device which opens in the body into an X, thanks to the use of a shape memory set around 37° C., each leg being implanted in a calibrated hole.

In practice, such a system does not allow proper introduction into the bone. This is because the preparation of 2 parallel holes in a phalange is extremely difficult due to the limited size and, above all, the parallel legs tend to open naturally during introduction and thereby exert an effect of distraction of the two fragments rather than compression.

Furthermore, the use of shape memory is very limiting due to the demands it makes on surgeons, in particular of temperature management: the implant must be fitted into the bone when cold before it warms and opens. This requires placing the implant in a support, storing it cold, and using all possible speed for implantation.

Finally, since the legs are straight, their shape memory tends to create a local support at their tips, which does not ensure satisfactory behavior and can damage the bone.

U.S. 2008/0177262 teaches a system for easier introduction whether by the shape (eye) or by a support or a clamp that keeps the legs of the implant closed during introduction.

Nevertheless, these systems do not operate very dependably, because they do not define the optimal criteria allowing proper introduction into the bone and good anchorage: the anchoring zones always tend to open too early, thereby blocking introduction.

OBJECT OF THE INVENTION

It is the object of the invention to remedy all these drawbacks simply, reliably, effectively and efficiently.

The problem that the invention proposes to solve is to define the success criteria for an intramedullary implant, easy to place and effective for generating primary and secondary stability of the osteosynthesis or arthrodesis focus thanks to its stiffness and its compression component.

SUMMARY OF THE INVENTION

The inventive implant is characterized in that it comprises two bone anchoring zones on either side of a stiff stability zone, withstanding shear forces, these two anchoring zones having a possibility of high deformation at their base (in particular by elasticity) and a design such that they can adopt a closed position (in particular thanks to a suitable clamp closed at their base) for easy introduction into a calibrated centromedullary hole (prepared with an appropriate instrument), and in that owing to this particular configuration, they offer in the bone site the possibility of obtaining the final impaction without a distraction effect on the bone and sufficient expansion to ensure proper fixation in the bone.

The anchoring zones can be deformed at their base by elasticity, superelasticity or shape memory and typically consist of branches or legs, optionally connected (olive or rugby ball shape). In the open shape, these branches have an outward positive angle at their base and are curved inwardly toward their tips, whereas when the shape is closed, the angle of the base is reversed, that is negative or turned inwardly, thereby obtaining the width at the tips (impaction side) that is smaller than their base, in order to avoid impaction in the bone and blocking of the penetration of the implant.

The invention has a particularly advantageous application, which cannot however be considered as limiting, for the preparation of arthrodeses in the phalanges of the fingers and toes, especially for the proximal and distal interphalangeal joints in the hand and foot.

The device is implantable via the dorsal path (or optionally lateral or palmar/plantar), but without pulpar approach, thereby minimizing the risks of infection and improving the patient's comfort.

To take account of the anatomical features, the anchoring zones are connected to the median zone serving for strength (in particular shear) at the osteosynthesis focus by more or less long connecting zones, and the central zone may have a bend to adapt to the characteristics of the desired arthrodesis.

The material constituting the implant of the invention must allow a certain minimal opening of the anchoring zones once the implant is in the body. It may therefore be made from any sufficiently elastic implantable material such as stainless steel, titanium, a bioresorbable material such as polylactide acid PLLA.

Preferably, the implant of the invention is prepared from a shape memory material used for its property of superelasticity (or elasticity associated with the transformation of the austenite martensite phase under stress) which has the widest known elasticity range (up to 8% in elastic elongation equivalent in traction for an implant of Nitinol, a nickel-titanium alloy comprising about 55.5 to 56% by weight of nickel, the remainder being titanium).

It is also possible to use a material having a thermal shape memory around 37° C.

BRIEF DESCRIPTION OF THE DRAWINGS

The invention is described in greater detail below in conjunction with the appended drawings in which.

SPECIFIC DESCRIPTION

Figure 2:
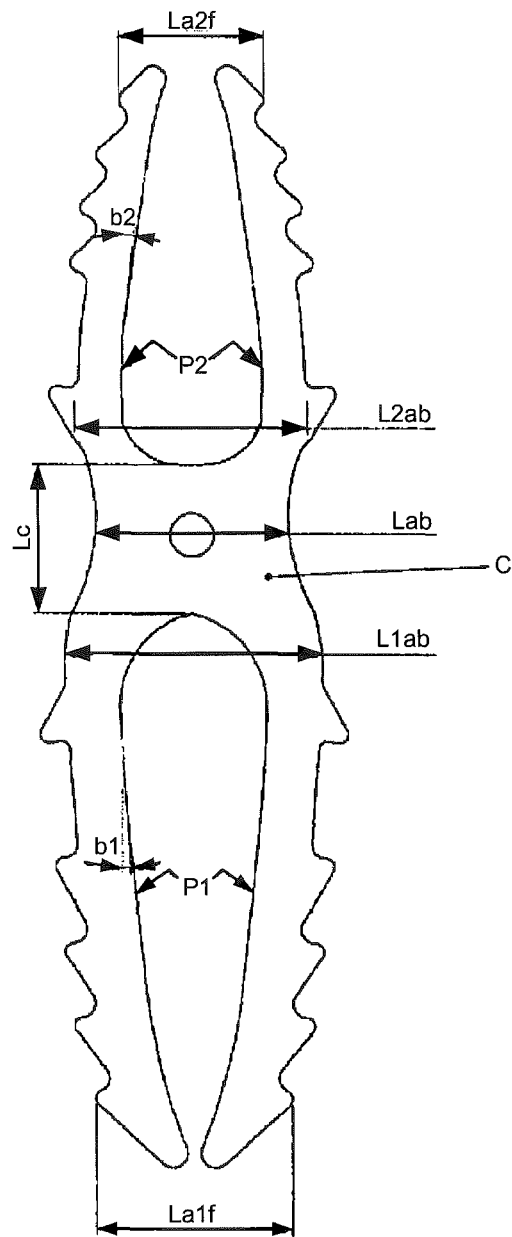
FIG. 2 shows the same example in its closed introduction position in its main plane.
Figure 3:
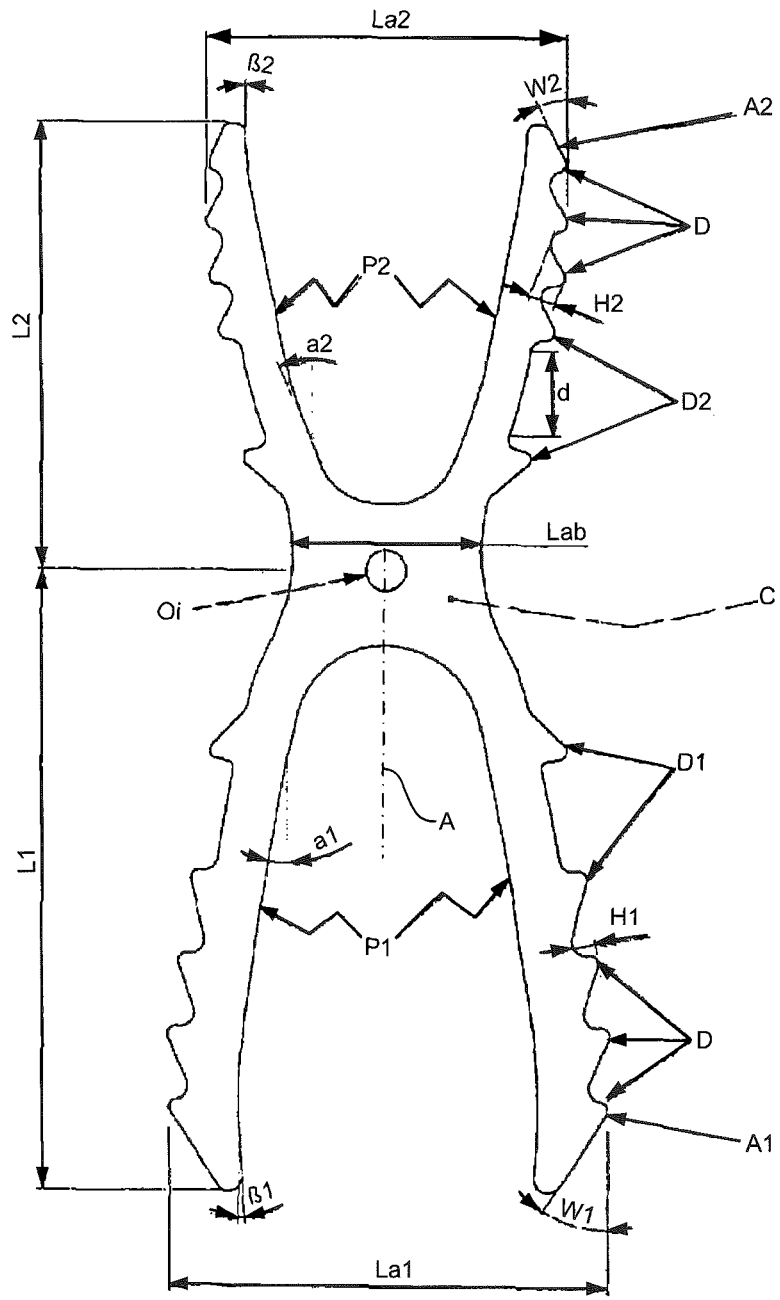
FIG. 3 shows an exemplary implant of the invention in its full open position, in its main plane.

The implant is in the form of 2 anchoring zones A1 and A2 connected by a central zone C (FIG. 1) and optionally intermediate connecting zones such that in the closed position, the shape is substantially inscribed in a very elongated rectangle (FIG. 2), and in the open shape, corresponds to a wider X-shape due to the spreading of the anchoring zones A1 and A2 (FIG. 3).

The anchoring zones A1 and A2 each have two legs P1 and P2 having lengths L1 and L2 (FIG. 3).

Figure 1:
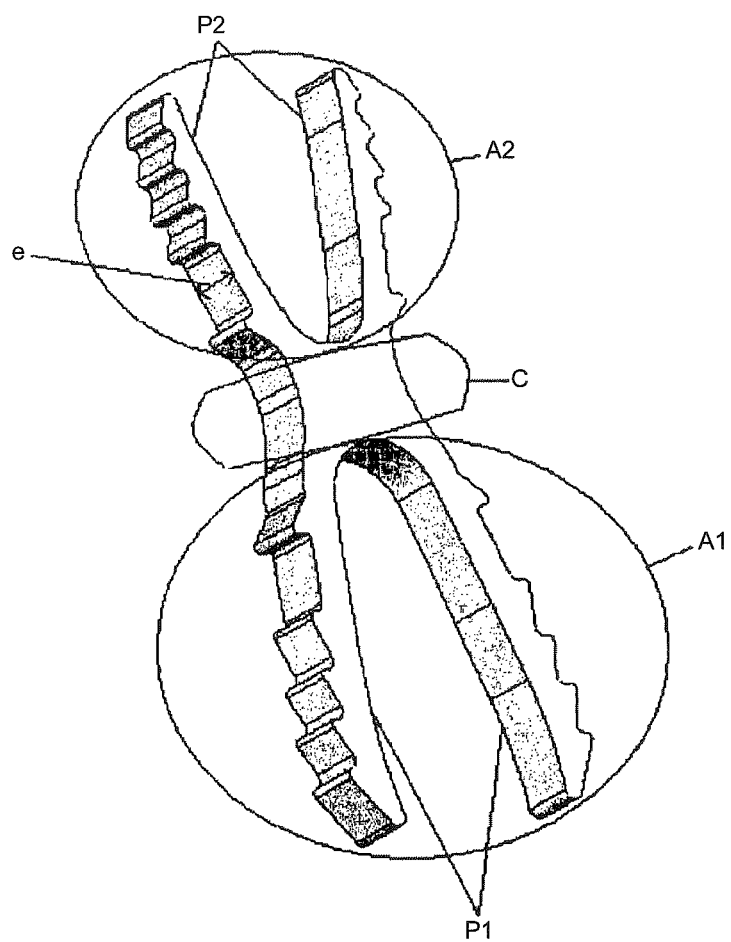
FIG. 1 shows an exemplary implant of the invention in its full open position in 3 dimensions.

The cross-section of the implant is adapted to the implantation sites, but preferably flat in order to have good mechanical strength and reduced size (typically the thickness e is about 1 to 2 mm) (FIG. 1).

FIG. 2 shows the closed position with the various widths of the implant: Lab is the width of the central zone C, L1$ab$ and L2$ab$ are the widths at the base of the anchoring zones A1 and A2. These 3 widths may be equal or slightly different to adapt to the bone site. Typically, the widths are about 2 to 5 times the thickness (or 2 to 10 mm). These dimensions are adapted to the various dimensions of the hand and foot but are not limiting because they depend on the bone site of the operated patient.

The anchoring zones A1 and A2 are suitable for separation by elastic effect or by shape memory effect at their base, so that the maximum width in the open position at the tips La1 and La2 (FIG. 3) is at least equal to the width of the base of the same anchoring zone in the closed position plus 50% minimum, or plus a minimum of 1.5 mm. This means that La1>L1$ab$+50% or La1>L1$ab$+1.5 mm and that La2>L2$ab$+50% or La2>L2$ab$+1.5 mm. This opening criterion is necessary to have sufficient fixation in the bone.

As shown in FIG. 3, the legs P1 and P2 are substantially straight at their base (on about ⅓ to half of their length) and are then rounded inwardly at their tips (on about ⅓ to half of their length). In the open position, the straight inner portions of the legs P1 and P2 make positive outward angles a1 and a2 with the longitudinal implant axis A (FIG. 3), whereas in the closed position, these angles become inward negative angles b1 and b2 (FIG. 2). The upper or outer portions (toward the tip) of the legs P1 and P2 virtually undergoes no particular deformation between the two open and closed shapes.

This particular geometric arrangement ensures that in the closed position, the legs virtually touch at the tips (FIG. 2), and that the widths at the tips in the closed position La1$f$ and La2$f$ are lower than the widths at the respective bases L1$ab$ and L2$ab$, thereby allowing easy introduction without distraction of the distal bone fragment and also obtaining the opened/closed movement by a local deformation at the base of the legs, that is by leaving the distal zone free for introducing this zone into the bone.

In order to obtain both easy introduction and sufficient opening movement, the angles a1 and a2 are preferably between +5 degrees and +25 degrees and the angles b1 and b2 between 0 degrees and −15 degrees.

Preferably, the width of the tips of the anchoring zones in the closed position La1$f$ and La2$f$ are lower than the widths of the bases of the zones L1$ab$ and L2$ab$, minus 20%: La1$f$<L1$ab$−20% and La2$f$<L2$ab$−20%.

The legs or anchoring zones are thus "articulated" at their base, and can therefore be secured in the closed position on a support or even better a clamp, positioned at an appropriate location defined in particular in the case of an elastic material (for a shape memory material, this is not absolutely necessary since the shape does not change as long as the activation temperature is not reached), this clamp not covering more than half of the length of the legs, thereby allowing introduction of at least half of the implant into its recess.

The inside tangents at the tip of the legs P1 and P2 in the open position make angles β1 and β2 with the longitudinal axis A of the implant close to 0 degrees, in order to have a good bone contact area along the whole lengths of the legs in the open position and to prevent the bone from being touched by the tips alone (FIG. 3).

In the implant site, at body temperature, the implant can still be in the closed position, or parallel or with semiopen legs so that the force exerted by opening of the legs is transmitted to the bone and ensures proper fixation.

This "olive" arrangement of the legs, associated with an "articulation" of the base and associated with a minimal introduction of half of their length allows completion of the insertion, once the clamp has been removed.

In order to guarantee satisfactory operation, the elasticity or memory of the piece must allow a transition from the closed shape (typically width 2 to 4 mm according to the size of the site) to an open shape with a significant movement (+1.5 to +3 mm approximately).

Similarly, the force of expansion of the legs (or swelling of the olive) must be significant: typically 1 to 3 kg for an arthrodesis of the tips (force measured at 37° C. in the blocked introduction position), without being excessive: it is important for the legs to avoid opening completely and for the bone to resist so as to have a real holding force.

The legs P1 and P2 or fins may have a rough surface or even better notches D (FIG. 3) on their outer surfaces intended to be press into the spongy bone and form a good anchorage. The typical depth of these notches H1 and H2 is about 0.5 mm. The opening of the legs must be at least 1.5 times this depth in order to ensure good engagement of the notches in the bone or 1.5 mm.

The legs P1 and P2 may also have a surface covered with an osseointegration coating such as hydroxyapatite (HAP) intended to facilitate the anchorage.

To facilitate introduction into the bone, the tips of the legs P1 and P2 are bevelled with an inward angle to the longitudinal axis A of the implant W1 and W2 (FIG. 3). This angle is typically between −20 degrees and −40 degrees.

By tests on fresh cadavers and experience, an optimal level of the force was determined with a minimum allowing anchorage of the notches in the spongy bone and a maximum force to be certain to avoid damaging the implantation site.

After tests and experience, an ideal zone was found with a maximum 20% of the elastic limit of the bone measured in a blocked closed shape at 37° C., which, considering the dimensions of the implant, gives rise to maximum values of about 3 kg, and the need for a rapid lowering as soon as the anchorage is obtained, or a force divided by 2 in the semi-open position (a force of 0.5 to 1.5 kg allows good holding). In fact, if the opening force is higher than about 3 kg, introduction into the bone becomes much more difficult, or even impossible above 4 kg. Finally, in order to guarantee a damage-free site, it is necessary for the force to become negligible for a virtually complete opening. These values are indicative and depend on the arthrodesis site and the bone quality.

In one version of the invention, the notches D1 and D2 on the outside of the legs P1 and P2 allow the positioning of a clamp and introduction at the base of the legs P1 and P2 (FIG. 3). These notches are symmetrical by pairs of legs and their spacing d is the same on the legs P1 and on the legs P2.

The central zone C must have a minimum length Lc equal to the length d between the notches D1 and D2 so that even in case of movement of the implant during final impaction, this zone C remains in the arthrodesis focus and performs its resistance function.

In one version of the invention, an orifice Or is provided in this central zone for positioning a holding pin to prevent migration of the implant at the time of final impaction.

Figure 4:
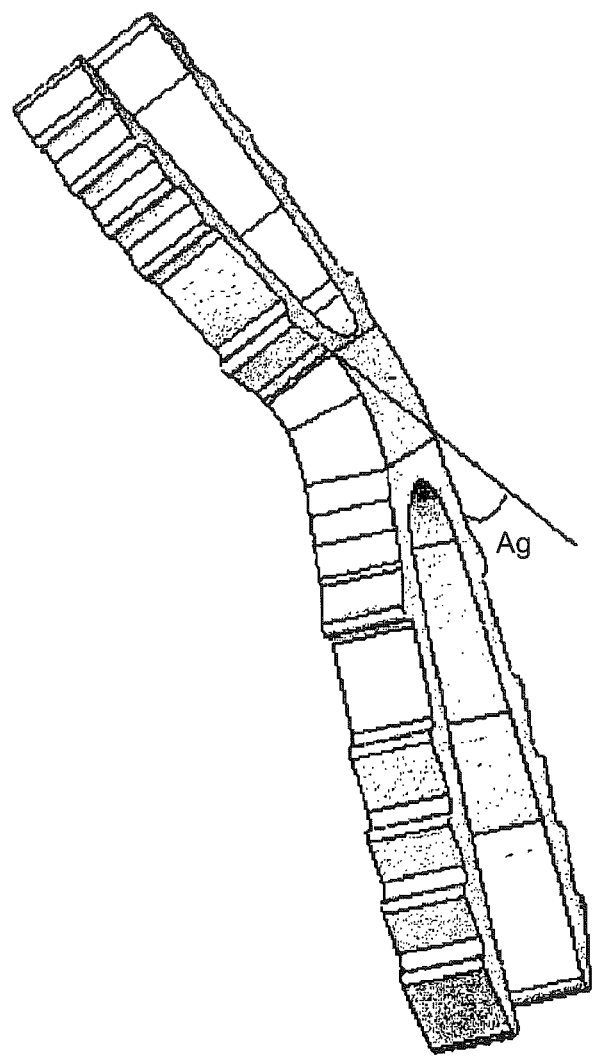
FIG. 4 shows an example of a bent implant according to the invention in its full open position, FIG. 5 (5a to 5f) shows the implantation sequence: closed, half introduced still stressed, fully introduced on one side (free in the bone), and the same sequence on the other side.

As shown in FIG. 4, this central zone may be bent at an angle Ag defined between the 2 main planes formed by the legs P1 on the one hand and P2 on the other hand to adapt to the surgical requirements for adjusting the position of the arthrodesis. In most cases, the angle Ag is fixed between 0° (typically flat position for an index) and 30° (typically for a little finger).

As an example, an operating technique of implantation of the inventive device for the case of an elastic or superelastic implant is described as follows as shown in FIG. 5:

DETAILED DESCRIPTION OF THE FEATURES OF THE INVENTION AND EXEMPLARY EMBODIMENTS

Figure 5A:
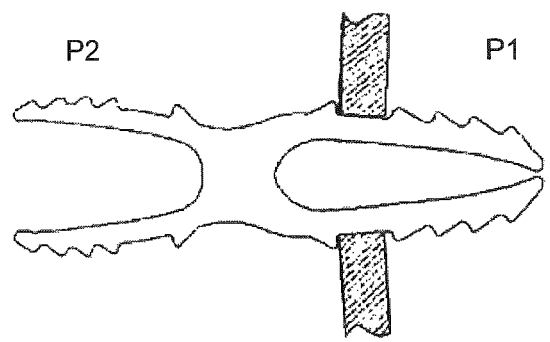
Figure 5B:
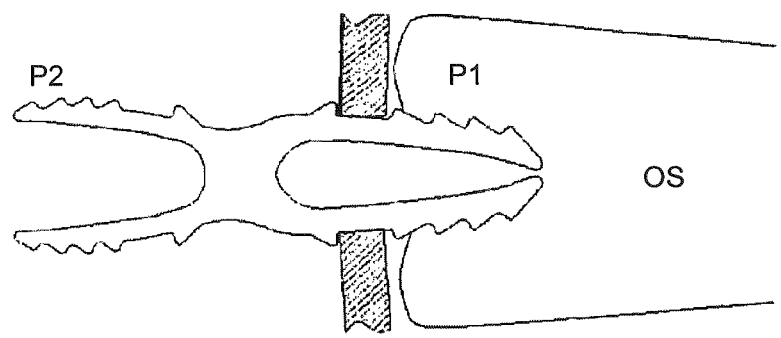
Figure 5C:
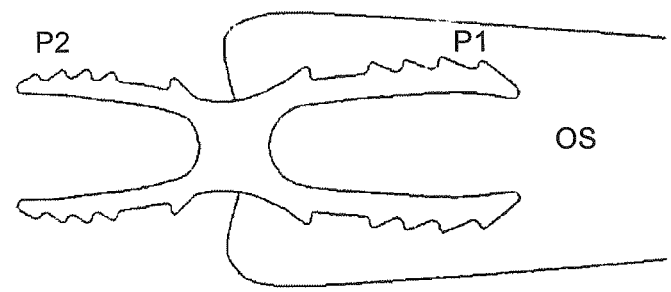
Figure 5D:
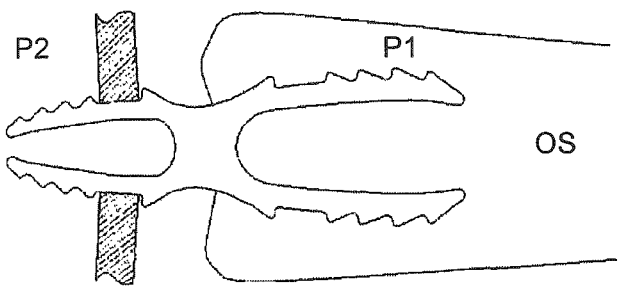
Figure 5E:
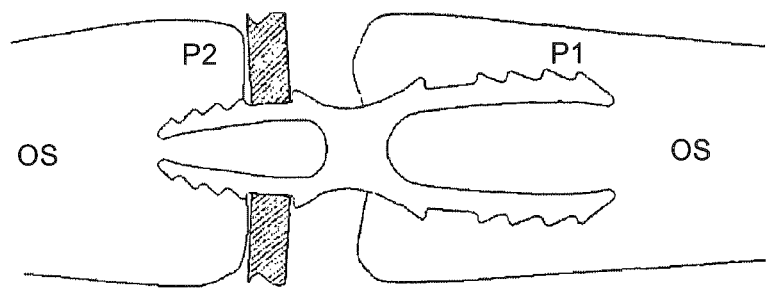
Figure 5F:
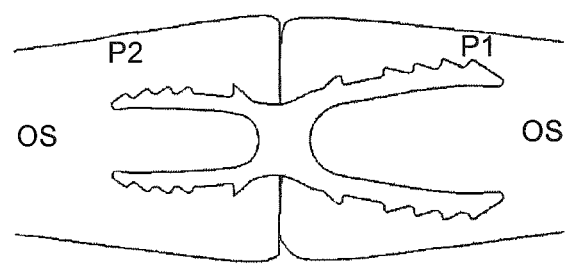

Approach by dorsal path
Resection of cartilages and osteophytes
Centromedullary perforation using an appropriate instrument to make a calibrated rectangular hole having a width of substantially L1ab or L2ab and thickness of substantially e (by a suitable rasp)
Closure of the clamp side P1 (FIG. 5a)
Implant introduction side P1 to minimum half (FIG. 5b)
Clamp removal
Complete introduction side P1 (FIG. 5c)
Closure of the clamp side P2 (FIG. 5d)
Placement of the bone side P2 on the implant side P2 to about half (FIG. 5e)
Removal of the clamp
Manual impaction of the bone side P2 on the bone P1 (FIG. 5f)

In a particular embodiment, intended for a distal interphalangeal arthrodesis (hand), the implant is prepared from a superelastic Nitinol alloy (nickel-titanium in the weight proportion 55.8% nickel and 44.2% titanium).

The cross-section of the central zone C is Lab×e=2.8×1.2 mm and the legs are asymmetrical to adapt better to the shapes of the bone, minimize the implanted metal section and allow sufficient expansion for good anchorage. The length of the legs is L2=6.5 mm distal side P2 and L1=9 mm proximal side P1. The length of the central zone C is 3 mm, allowing a slight offset during closure, without affecting the shear strength. To adapt to the surgeon's choice, this central zone may be bent (typically flat or 15° or 25°.

In the closed position, the width of the proximal base L1ab is 3.8 mm and of the distal base L2ab is 3.0 mm. The opening of the legs P1 and P2 is 2.5 mm or 2.2 mm, that is La1 is 6.3 mm and La2 is 5.2 mm. In the open position the angle at the base of the legs is a1=10° and a2=22°. The straight portion is about 45% of the total length. The curvature of the distal tip of the legs is calculated so that the angle of the tangent at the tip is $\beta1=-5°$ and $\beta2=-3°$. In the closed position, the angle at the base of the legs is b1=−4°, b2=−2°. And the width at tip is La1f=2.5 mm and La2f=2.1 mm.

In one embodiment of the invention, the 0.5 mm deep notches are distributed on the legs (1 notch at approximately 0.8 mm spacings).

The angle of incidence of the tip of the legs (including notches) is w1=33° and w2=24°, allowing easy introduction without the distraction effect between the two bone pieces to be osteosynthesized.

The rounded design of the anchoring zones serves to obtain a maximized contact area over the entire length in the open shape, with an impaction effect in the spongy bone, and hence a spongy packing effect.

In another example, more appropriate for arthrodesis of the thumb, the dimensions are rather the following: Closed widths: L1ab=6.5 mm, L2ab=5 mm, with an opening of 3 to 4 mm approximately to obtain: La1=11 mm and La2=8 mm and L1=13 mm and L2=9 mm.

The invention claimed is:

1. An intramedullary osteosynthesis or arthrodesis implant comprising:
    a central body;
    a first pair of legs extending from the central body, each leg having a base, a leg tip and an outer surface extending from the base to the leg tip and facing away from the other leg of the pair of legs, the leg base of each leg including a base notch on the outer surface shaped to face in a first direction and the leg tip of each leg including two or more tip notches on the outer surface spaced from one another a first distance, each tip notch shaped to face in a second direction different from the first direction, and each leg including a flat surface extending along the outer surface a second distance between the base notch and the tip notch nearest the base notch, wherein the second distance is longer than the first distance; and
    a second pair of legs extending from the central body in a direction opposite the first pair of legs.

2. The implant of claim 1, wherein the central body, first pair of legs and second pair of legs are positioned along a longitudinal axis.

3. The implant of claim 1, wherein each leg of the second pair of legs has a leg base and a leg tip, the second pair of legs, measured from the leg base to the leg tip, has a shorter length than the first pair of legs, measured from the leg base to the leg tip.

4. The implant of claim 1, wherein each leg of the second pair of legs has a leg base and a leg tip, each leg base including a base notch and each leg tip including a tip notch.

5. The implant of claim 4, wherein each leg of the first and second pairs of legs includes two or more tip notches.

6. The implant of claim 1, wherein the second pair of legs include an inward curve along the length of each leg towards the tip of each leg.

7. An intramedullary osteosynthesis or arthrodesis implant comprising:
    a monolithic body extending along a longitudinal axis, the body including a plurality of notches on an outward-facing surface of the body, at least a first notch is spaced from a second notch in a direction along the axis, the first and second notches extending outwardly in the same direction from the axis, a third notch and a fourth notch extending outwardly in the same direction from the axis as the first and second notches, and at least the first notch having a taper along the axis in a different direction than a taper of the third notch along the axis, the first and second notches spaced a first distance from one another and the fourth notch spaced a second distance from the first or second notch that is closer to the fourth notch, wherein the second distance faces the same direction as the first, second, third and fourth notches and is free of notches and is larger than the first distance.

8. The implant of claim 7, wherein the monolithic body further comprises a central body, a first pair of legs and a second pair of legs, wherein a base of each of the first and second pair of legs is adjacent the central body.

9. The implant of claim 8, wherein the second pair of legs extends from the central body in a direction opposite the first pair of legs.

10. The implant of claim 9, wherein the central body, first pair of legs and second pair of legs are positioned along the longitudinal axis.

11. The implant of claim 7, wherein the second pair of legs, measured from the leg base to a leg tip, has a shorter length than the first pair of legs, measured from the leg base to the leg tip.

12. The implant of claim 7, wherein each leg of the second pair of legs includes at least one notch.

13. The implant of claim 12, wherein one leg of the first pair of legs includes the first and second notches and the other leg of the first pair of legs includes the third notch.

14. The implant of claim 7, wherein the second pair of legs include an inward curve along the length of each leg towards the tip of each leg.

15. An intramedullary osteosynthesis or arthrodesis implant comprising:
    a monolithic body including a first pair of legs and a second pair of legs, each leg of each pair of legs having a base, a tip, and an outer surface extending from the base to the tip and facing away from the other leg of the pair of legs, the second pair of legs, measured from the leg base to the leg tip, has a shorter length than the first pair of legs, measured from the leg base to the leg tip, and each leg of the first and second pair of legs including two or more tip notches on the outer surface at each leg tip, the two notches spaced from one another a first distance, and a surface free of notches extending along the outer surface a second distance from the two or more tip notches towards a base notch on the outer surface, wherein the second distance is greater than the first distance.

16. The implant of claim 15, wherein the base notch is shaped to face in a first direction and the tip notches shaped to face in a second direction different from the first direction.

17. The implant of claim 15, wherein the first pair of legs and the second pair of legs both extend from a central body.

18. The implant of claim 17, wherein the central body, first pair of legs and second pair of legs are positioned along a longitudinal axis.

19. The implant of claim 15, wherein each leg of the second pair of legs includes a base notch and two or more tip notches.

20. The implant of claim 19, wherein each leg of the first and second pairs of legs includes three or more tip notches.

* * * * *